(12) United States Patent
Burton et al.

(10) Patent No.: US 7,479,486 B2
(45) Date of Patent: Jan. 20, 2009

(54) SULPHUR ANALOGUES OF 21-HYDROXY-6,19-OXIDOPROGESTERONE (21OH-6OP) FOR TREATING EXCESS OF GLUCOCORTICOIDS

(75) Inventors: Gerardo Burton, Florida (AR); Carlos P. Lantos, Buenos Aires (AR); Adriana Silvia Veleiro, Martinez (AR)

(73) Assignee: Laboratoires Serono SA, Vaud (CH)

( * ) Notice: Subject to any disclaimer, the term of this patent is extended or adjusted under 35 U.S.C. 154(b) by 0 days.

(21) Appl. No.: 11/123,206

(22) Filed: May 6, 2005

(65) Prior Publication Data

US 2005/0222104 A1 Oct. 6, 2005

Related U.S. Application Data

(62) Division of application No. 10/363,860, filed as application No. PCT/EP01/10750 on Sep. 17, 2001, now Pat. No. 7,053,228.

(30) Foreign Application Priority Data

Sep. 18, 2000 (EP) .................................. 00119495

(51) Int. Cl.
*A61K 31/56* (2006.01)
*C01J 7/00* (2006.01)
*C07J 53/00* (2006.01)
*C07D 333/02* (2006.01)

(52) U.S. Cl. ........................... 514/180; 514/181; 540/5; 540/56; 549/41; 552/510; 552/512

(58) Field of Classification Search ................. 514/179, 514/180, 181; 552/510, 512, 572, 541; 549/41, 549/29; 540/5, 56
See application file for complete search history.

(56) References Cited

U.S. PATENT DOCUMENTS

| 6,303,591 | B1 * | 10/2001 | Burton et al. ................ 514/179 |
| 7,053,228 | B2 * | 5/2006 | Burton et al. ................ 552/512 |
| 7,071,328 | B2 * | 7/2006 | Burton et al. .................. 540/5 |
| 2004/0029846 | A1 | 2/2004 | Burton et al. |
| 2004/0092733 | A1 | 5/2004 | Burton et al. |

FOREIGN PATENT DOCUMENTS

| EP | 0 348 910 | 1/1990 |
| EP | 0 903 148 | 3/1999 |

OTHER PUBLICATIONS

Synthesis of 21-hydroxy-11,19-oxidopregn-4-ene-3,20-dione and 21-hydroxy-6,19-oxidopregn-4-ene-3,20-dione; Steroids, vol. 60, No. 3, pp. 268-271, 1995.*

"Synthesis of 21-hydroxy-11, 19-oxidopregn-4-ene-3,20-dione and 21-hydroxy-6, 91-oxidopregn-4-ene-3, 20-dione"; *Steroids*, vol. 60, No. 3, pp. 268-271, 1995.

Burton et al.: "21-hydroxy-6,19-oxidoprogesterone: A novel synthetic steroid with specific antiglucocorticoid properties in the rats" Molecular Pharmacology, vol. 52, No. 4, pp. 743-753, Oct. 1, 1997.

D.B. Gowan: "Modifiers of steroid-hormone metabolism: A review of their chemistry, biochemistry and clinical applications" J. Steroid Biochem., vol. 5, pp. 501-523, 1974.

Barry Forman et al.: "Nuclear hormone receptors activate direct, inverted, and everted repeats" Annals of New-York Academy of Science, vol. 761, pp. 29-37, 1995.

Jeffrey L. Arriza et al.: "Cloning of human mineralocorticoid receptor complementary DNA: Structural and functional kinship with the glucocorticoid receptor" Science, vol. 237, pp. 268-275, 1987.

G. Teutsch et al.: "General structure-activity correlations of antihormones" Annals of New-York Academy of Science, vol. 761, pp. 5-28, 1995.

VIII International Congress of Pharmacology, Tokyo, Japan Abstract, 1981.

Irvin M. Spitz et al.: Mifepristone (RU 486)—A modulator of progestin and glucocorticoid actions: N. Engl. J. Med., vol. 329, pp. 404-412, 1993.

Carlos P. Lantos et al.: "Structure-activity relationship in certain glucocorticoids and mineralcorticoids" Physiopathology of Endocrine Diseases and Mechanisms of Hormone Actions, pp. 477-494, 1981.

G. Burton et al.: "Sodium-retaining activity of some natural and synthetic 21-deoxysteroids" Mol. Pharmacol., vol. 47, pp. 535-543, 1995.

Adriana L. Brachet-Cota et al.: "An improved preparation of 11,19-oxidopregn-4-ene-3,20-dione and 6,19-oxidopregn-4-ene-3,11,20-trione" Z. Naturforsch., vol. 45b, pp. 711-715, 1990.

Mario D. Galigniana: "Stability study on renal type I mineralocorticoid receptor" Life Science, vol. 59, pp. 511-521, 1996.

Christina R. McKittrick et al.: "Regulation of serotonergic function in the CNS by steroid hormones and stress" CNS Neurotransmitters and Nuromodulators, Neuroactive Steroids, pp. 37-76.

W.L. Duax et al.: "The mechanism of action of steroid antagonists: insights from crystallographic studies" J. Steroid Biochem., vol. 31, No. 48, pp 481-492, 1988.

David H. Wagner, Jr., et al.: "Rescue of thymocytes from glucocorticoid-induced cell death mediated by DC28/CTLA-4 costimulatory interactions with B7-1/B7-2" J. Exp. Med., vol. 184, pp. 1631-1638, No. 1996.

* cited by examiner

*Primary Examiner*—Sabiha Qazi
(74) *Attorney, Agent, or Firm*—Oblon, Spivak, McClelland, Maier & Neustadt, P.C.

(57) ABSTRACT

The present invention is related to novel 21-hydroxy-6,19-oxidoprogesterone (21OH-6OP) analogues, their use as antiglucocorticoids for the treatment and/or prophylaxis of disease associated to an excess of glucocorticoids. In particular, the invention relates to the use of novel 21-hydroxy-6,19-oxidoprogesterone (21OH-6OP) analogues for treating Cushing's syndrome, iatrogenic hypercortisolism or depression. Also the present invention is related to methods of preparing the novel 21-hydroxy-6,19-oxidoprogesterone (21OH-6OP) analogues.

2 Claims, 5 Drawing Sheets

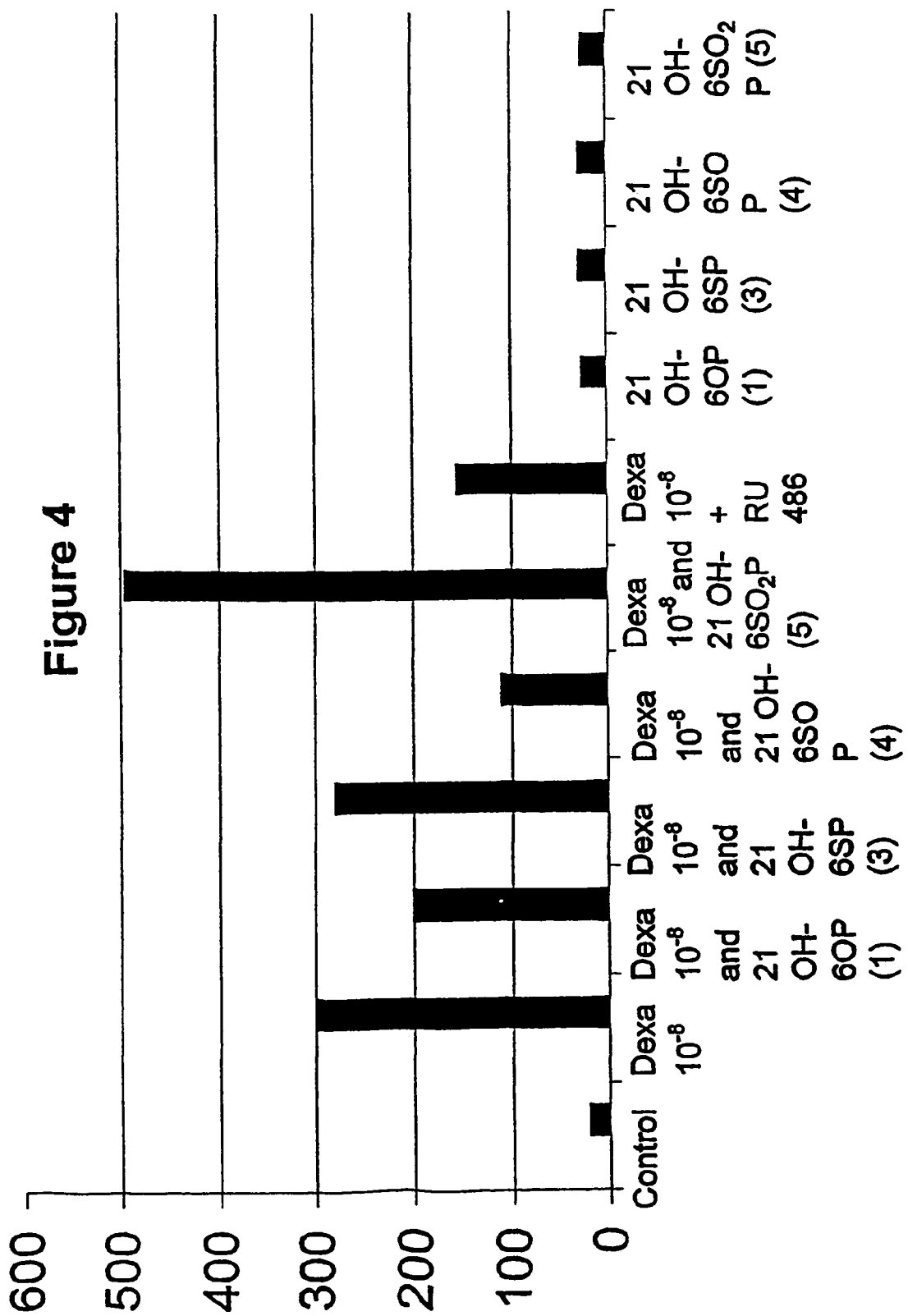

SULPHUR ANALOGUES OF 21-HYDROXY-6,19-OXIDOPROGESTERONE (21OH-6OP) FOR TREATING EXCESS OF GLUCOCORTICOIDS

This application is a Division of U.S. application Ser. No. 10/363,860, filed Aug. 20, 2003, now pending; which is a National Stage of PCT/EP01/10750, filed Sep. 17, 2001. In addition, priority is claimed to European patent application 00119495.0 filed Sep. 18, 2000.

FIELD OF THE INVENTION

The present invention is related to novel 21-hydroxy-6,19-oxidoprogesterone (21OH-6OP) analogues, their use as anti-glucocorticoids for the treatment and/or prophylaxis of diseases associated to an excess of glucocorticoids. In particular, the invention relates to the use of novel 21-hydroxy-6,19-oxidoprogesterone (21OH-6OP) analogues for treating Cushing's syndrome, iatrogenic hypercortisolism or depression. Also the present invention is related to methods of preparing the novel 21-hydroxy-6,19-oxidoprogesterone (21OH-6OP) analogues.

BACKGROUND OF THE INVENTION

Corticosteroids are steroid hormones related structurally to cholesterol. These hormones are synthesized in the adrenal cortex and include the glucocorticoids (e.g. cortisol), the mineralocorticoids (e.g aldosterone) as well as weak androgens and estrogens. The adrenal function, like that of the thyroid gland, is under the control of the hypothalamus (HPT) and the pituitary (PIT). When cortisol (the naturally-occurring glucocorticoid) levels drop below a setpoint, the hypothalamus releases CRH (corticotrophin releasing hormone) which stimulates adrenocorticotropic hormone (ACTH) release from the pituitary. ACTH is a tropic hormone which stimulates the synthesis and secretion of cortisol (it has minimal effects on aldosterone synthesis/secretion), and the growth of the adrenal gland. When cortisol levels increase, this shuts off CRH and ACTH secretion (cf. FIG. 1).

Cortisol is characterized by its properties related to the biosynthesis and metabolism of glucose and properties related to non-specific as well as specific immunity. Due to their effects on the glucose metabolism, cortisol and natural or synthetic analogues thereof are usually named glucocorticoids. They bind to the glucocorticoid receptor (GR).

The glucocorticoid receptor is a member of a protein super family of closely related intracellular receptors which function as ligand-activated transcription factors. Other members of this super family are the mineralocorticoid receptor (MR) and the progesterone receptor (PR). MR and GR have shown to be highly homologous, thus natural and even synthetic steroids exhibit cross-reaction between these receptors. With respect to PR, its natural ligand progesterone also cross-reacts with MR and GR.

Cushing's syndrome is a disorder resulting from increased adrenocortical secretion of cortisol. Hyperfunction of the adrenal cortex may be ACTH-dependent or it may be independent of ACTH regulation, e.g. production of cortisol by an adrenocortical adenoma or carcinoma The administration of supraphysiologic quantities of exogenous cortisol or related synthetic analogs suppresses adrenocortical function and mimics ACTH-independent glucocorticoid hyperfunction. ACTH-dependent hyperfunction of the adrenal cortex may be due to hypersecretion of ACTH by the pituitary, secretion of ACTH by a nonpituitary tumor such as small cell carcinoma of the lung (the ectopic ACTH syndrome), or administration of exogenous ACTH. While the term "Cushing's syndrome" has been applied to the clinical picture resulting from cortisol excess regardless of the cause, hyperfunction of the adrenal cortex resulting from pituitary ACTH excess has frequently been referred to as Cushing's disease, implying a particular physiologic abnormality. Patients with Cushing's disease may have a basophilic adenoma of the pituitary or a chromophobe adenoma. Microadenomas can usually be visualized by CT or, preferably, MRI scan, using a high-resolution technique augmented by gadolinium. Some micro-adenomas are difficult to visualize even with these modalities. In some cases, no histological abnormality is found in the pituitary despite clear evidence of ACTH overproduction.

Reference to Cushing's syndrome is herein intended to mean the clinical picture resulting from cortisol excess regardless of the cause, which may be also iatrogenic, both by the injection of ACTH or by the direct administration of cortisol or synthetic analogs such as prednisone, prednisolone, dexamethasone or others that are widely used in various types of diseases including alergic, asthmatic, inflammatory or immunologic. Cushing's syndrome includes in addition adrenal tumours secreting corticoids, ectopic ACTH production and Cushing's disease.

Clinical manifestations include rounded "moon" faces with a plethoric appearance. There is truncal obesity with prominent supraclavicular and dorsal cervical fat pads ("buffalo hump"); the distal extremities and fingers are usually quite slender. Muscle wasting and weakness are present. The skin is thin and atrophic, with poor wound healing and easy bruising. Purple striae may appear on the abdomen. Hypertension, renal calculi, osteoporosis, glucose intolerance, reduced resistance to infection, and psychiatric disturbances are common. Cessation of linear growth is characteristic in children. Females usually have menstrual irregularities. An increased production of androgens, in addition to cortisol, may lead to hypertichosis, temporal balding, and other signs of virilism in the female.

Although development of antihormonal agents related to the estrogen and androgen receptors has been successful, the search for selective anti-corticoids is more restricted.

Known agents suppressing the synthesis of steroid hormones at various levels (i.e. inhibitors of enzymes which catalyze various stages of the synthesis of steroid hormones) are reviewed in *J. Steroid Biochem.*, vol. 5, p. 501 (1974) and include the following:

a) derivatives of diphenylmethane, e.g. amphenon B (which suppresses the synthesis of steroid hormones at stages 11-beta-, 17- and 21- of hydroxylase);

b) derivatives of pyridine (SU-c series), e.g. metirapon (which suppresses synthesis at stage 11-beta of hydroxylase);

c) substituted alpha, alpha-glutaramides, e.g. aminoglutetimide (which impedes the synthesis of pregnenolone from cholesterol through suppression of 20-alpha-hydroxylase and $C_{20}$, $C_{22}$-liase;

d) steroid substances e.g. trilostan (3 beta-substituted steroid-3 beta-hydroxy-5-androsten-17-one), which suppresses 3 beta-desoxysteroidhydrogenase-5.4 isomerase (*Steroids*, vol. 32, p. 257).

e) steroids of the spironolactone family which are used as rapidly dissociating anti-Mineralocorticoids (*PNAS USA* 71(4) p. 1431-1435 (1974)).

f) synthetic steroid described as an anti-Mineralocorticoids, ZK91587, showing specific binding properties for the kidney (*Z. Naturforsch.*, 45b, p. 711-715 (1990)) and hippocampus type I MR (*Life Science*, 59, p. 511-21 (1996)), but not for type II GR. It may therefore be conveniently useful as a tool in the investigation of MR function in tissues containing both receptor systems.

Agents that specifically suppress the interaction of glucocorticoid hormones with hormone receptors are:

a) Mifepriston (11β,17β)-11-[4-(Dimethylamino)phenyl]-17-hydroxy-17-(1-propynyl)estra-4,9-dien-3-one, which acts on receptors of glucocorticoid hormones to form a complex incapable of initiating mechanisms leading to glucocorticoid effect (*Annals of New York Academy of Science*, vol. 761, p. 296-310 (1995)); said compound is also known as a contragestive agent (RU38486 or RU486).

b) non-steroid substances (*J: Steroid Biochem.*, vol. 31, p. 481-492 (1988)) e.g. drotaverina hydrochloride (a derivative of isoquinoline-1-(3.4-dietoxibene zilidene)-6.7-dietoxy-1,2,3,4-tetrahydrizoquinoline) or acetyl-salicic acid (*Moskovskaya Meditsina*, 1990, "Receptor mechanisms of the glucocorticoid effect" by V. P. Golikov).

To-date, the only therapeutical application for antiglucocorticoids (e.g. Mifepristone) that has been attempted in a clinical setting is to treat inoperable cases of nonpituitary Cushing's syndrome. In the case of Mifepristone (both an anti-progesterone and an anti-glucocorticoid), high doses (up to 800 mg per day) are required. Employing a systematic application of strategies to increase activity and decrease cross-reactivity and undesirable side effects, impressive progress has been reported in the development of new antihormonal agents with greater potency and selectivity, especially in the antiestrogen and antiandrogen fields.

A further antiglucocorticoid agent is disclosed in EP-903, 146 which is related to a synthetic steroid, designated 21-hydroxy-6,19-oxidoprogesterone (21OH-6,19-OP), having the formula I

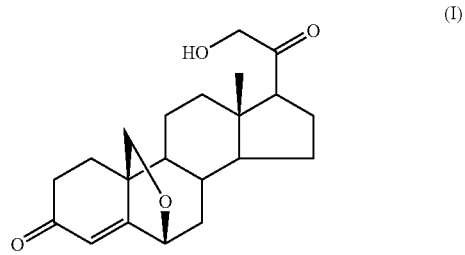

21OH,19-OP is reported to be a selective antiglucocorticoid and which does not substantially cross-react with uterus-PR or kidney-MR.

DESCRIPTION OF THE INVENTION

It is an object of the present invention to provide new antigluco-corticoid compounds.

It is a further objective of the present invention to provide a novel method of treating disease states associated with an excess of glucocorticoids.

In a first aspect, the invention provides a compound of formula (II):

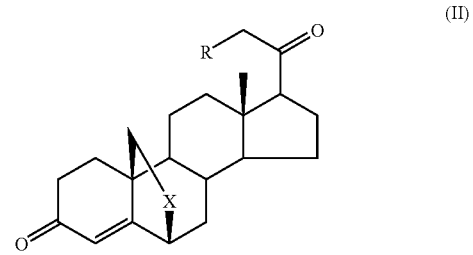

wherein X is S, SO and $SO_2$, and R is either H or OH.

In a second aspect, the invention provides a compound of formula (II)

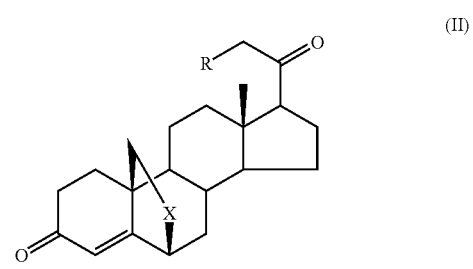

wherein X is S, SO and $SO_2$, and R is either H or OH for use as a medicament.

In a third aspect, the invention provides the use of a compound of formula (II)

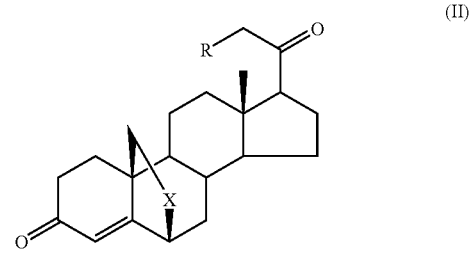

wherein X is S, SO and $SO_2$, and R is either H or OH, in the manufacture of a medicament for the treatment or prophylaxis of diseases associated to an excess of glucocorticoids.

In a fourth aspect, the invention provides a pharmaceutical composition comprising at least one 21-hydroxy-6,19-oxido-progesterone analog of formula II and one or more suitable carriers thereof.

In a fifth aspect, the invention provides a method for preparing a compound of the invention.

The new found compounds have a 6,19-sulfanyl-,6,19-sulfoxide- and 6,19-sulfone bridge instead of a 6,19-oxygen bridge within the 21-hydroxy-6,19-oxido-progesterone of formula (I). Thus, they represent the sulfur analogues (II) of the 21-hydroxy-6,19-oxidoprogesterone (I).

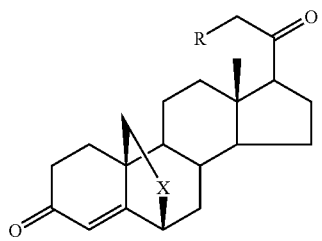
(II)

with X being S, SO and SO$_2$, while R is either H. or OH.

and more particularly sulfur analogues of the following Formula IIa

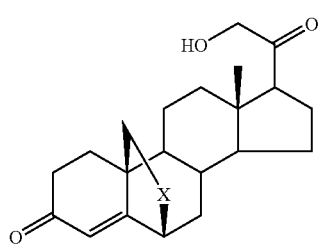
(IIa)

wherein X is SO or SO$_2$.

More specifically, the present invention is related to the following three 21-deoxy- and three 21-hydroxy-6,19-oxidoprogesterone analogues:

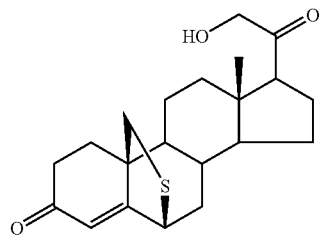
3

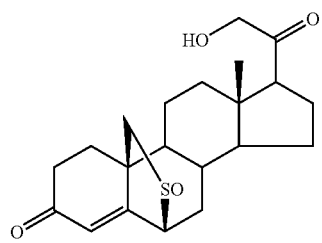
4

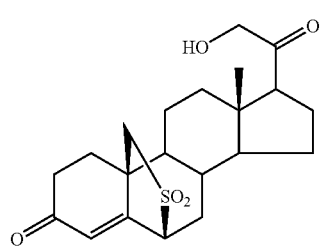
5

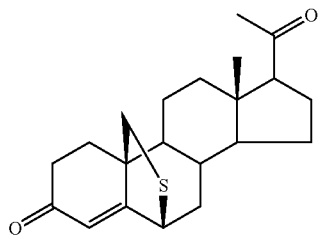
6

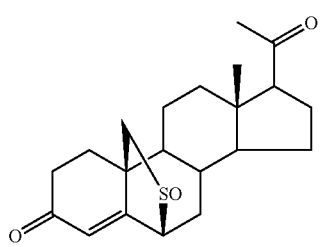
7

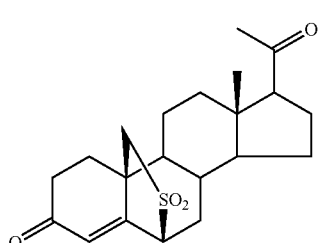
8

A further advantage of the compounds of the present invention is their convenient synthesis. In particular, the transformation of the sulfanyl bridge of compounds 3 and 6 to the sulfoxides 4 and 7 and the sulfones 5 and 8 by oxidation is quite convenient to be performed. Furthermore, the sulfoxide and the sulfone bridge improve the water solubility and stability of the compounds.

The antiglucocorticoids of the present invention are suitable for the treatment of diseases associated with an excess of glucocorticoids. In particular, the antiglucocorticoids of the present invention are useful for the treatment of Cushing's syndrome, iatrogenic hypercortisolism and depression, which are associated with an excess of glucocorticoids in the body, notably of mammals. They are also useful for treating disorders requiring modulation of the immune response.

The present invention, thus, provides the 21-hydroxy-6,19-sulfanyl, and sulfoxy- and sulfonyl-progesterones of formula II for use as a medicament.

It is a further object of the present invention to use the 21-hydroxy-6,19-sulfanyl, and sulfoxy- and sulfonyl-progesterones of Formula II in the manufacture of a medicament for the treatment or prophylaxis of diseases associated with an excess of glucocorticoids. More preferably, the compound of formula II is used in the manufacture of a medicament for the treatment of Cushing's syndrome, iatrogenic hypercortisolism, depression or modulating the immune response.

The compound of formula I may be formulated in accordance with usual steroid formula-tions with one or more suitable carriers thereof.

DESCRIPTION OF THE DRAWINGS

FIG. 3a illustrates the cell apoptosis induced in thymocytes by Dexamethasone alone ($10^{-8}$ M).

FIG. 3b illustrates the cell apoptosis induced in thymocytes by Dexamethasone ($10^{-8}$ M)+21OH-6OP ($10^{-5}$ M) (Compound (I)).

FIG. 3c illustrates the cell apoptosis induced in thymocytes by Dexamethasone ($10^{-8}$ M)+21OH-6SOP ($10^{-5}$ M) (Compound (4)).

FIG. 3d illustrates the cell apoptosis induced in thymocytes by Dexamethasone ($10^{-8}$ M)+RU-486 ($10^{-6}$ M).

FIG. 3e illustrates the cell apoptosis induced in thymocytes by Dexamethasone ($10^{-8}$ M)+21OH-6SP ($10^{-5}$ M) (Compound (3)).

FIG. 3f illustrates the cell apoptosis induced in thymocytes by Dexamethasone ($10^{-8}$ M)+21OH-6SO$_2$P ($10^{-5}$ M) (Compound (5)).

FIG. 4 refers to the reporter gene assay described below and displays activity of test compounds (1), (3), (4) and (5), used at $10^{-6}$M final concentration, to reference compound (RU 486). Dexa means dexamethasone, and RU 486 (11-(4-Dimethylamino-phenyl)-17-hydroxy-13-methyl-17-prop-1-ynyl-1,2,6,7,8,11,12,13,14,15,16,17-dodecahydro-cyclopenta[α]phenanthren-3-one) was used as positive control. Ordinates correspond to luciferase units/β-galactosidase units.

Figure 1:
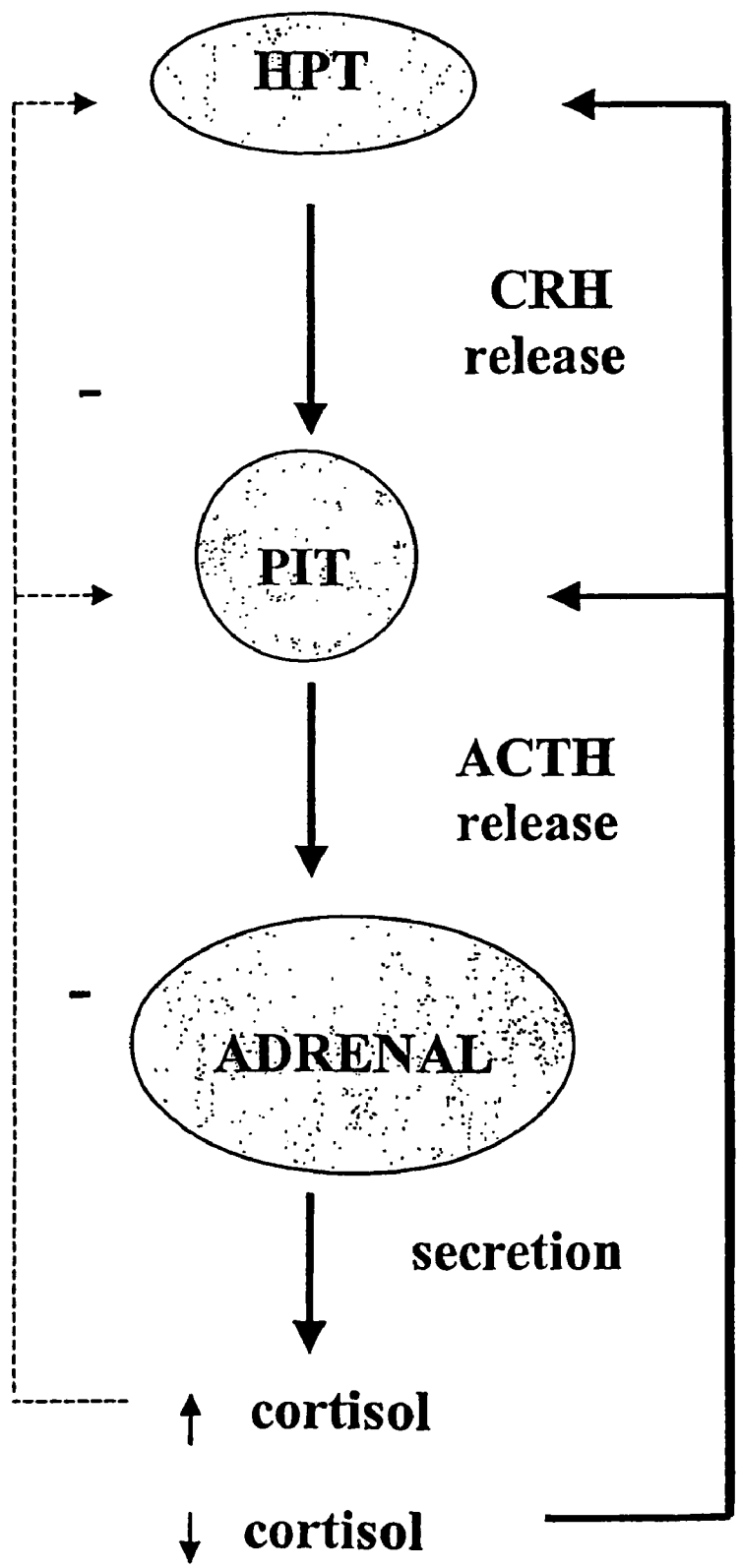
FIG. 1 illustrates the pathway relating to endogenous cortisol production.
Figure 2:
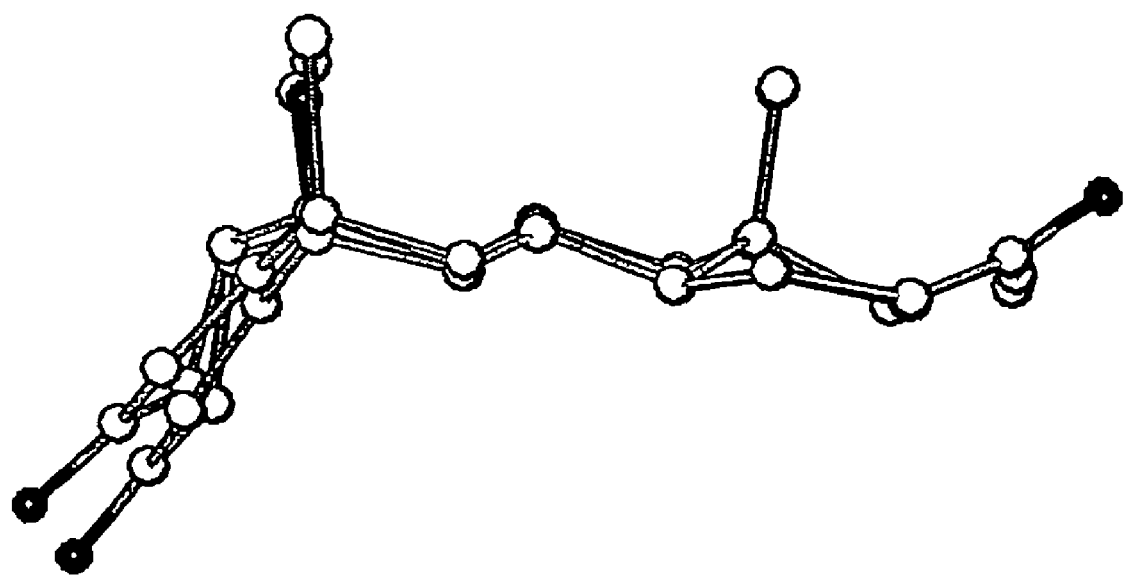
FIG. 2 shows a least squares overlay of X ray structures of 6,19-oxidoprogesterone (I) (6OP) and 6,19-sulfanyl-progesterone (6).
Figure 3A:
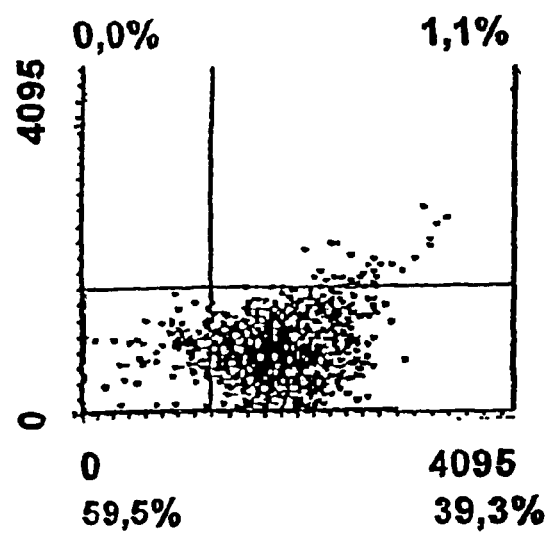
FIGS. 3a-3f show cytograms wherein GR-FL represents fluorescence from FITC and RD-FL represents fluorescence from propidium iodide (data obtained from the thymocyte apoptosis assay described below). Viable cells which do not bind annexin-FITC nor propidium iodide appear in the lower right quadrant. Necrotic or late apoptotic cells appear in the upper right quadrant.
Figure 3B:
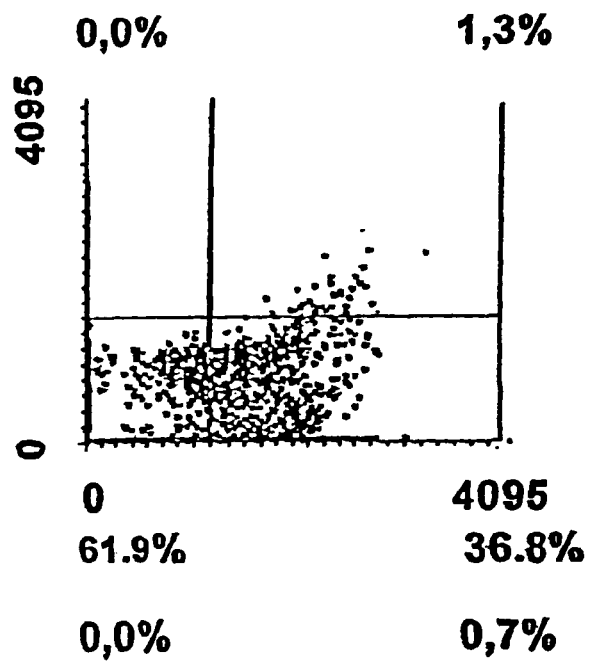
Figure 3C:
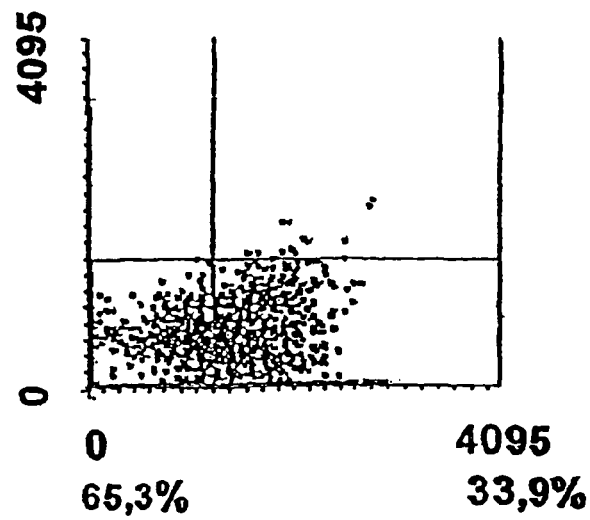
Figure 3D:
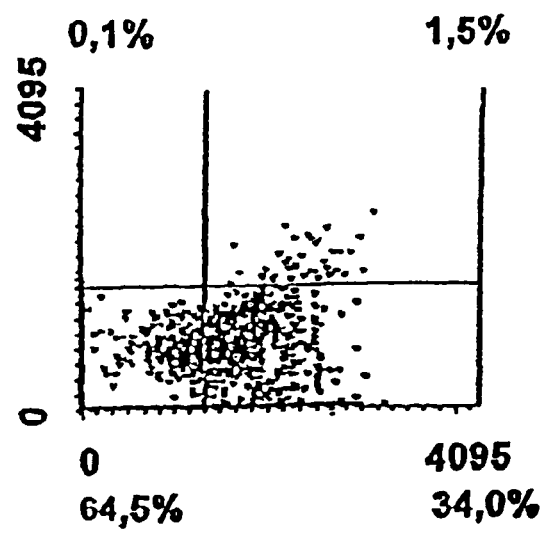
Figure 3E:
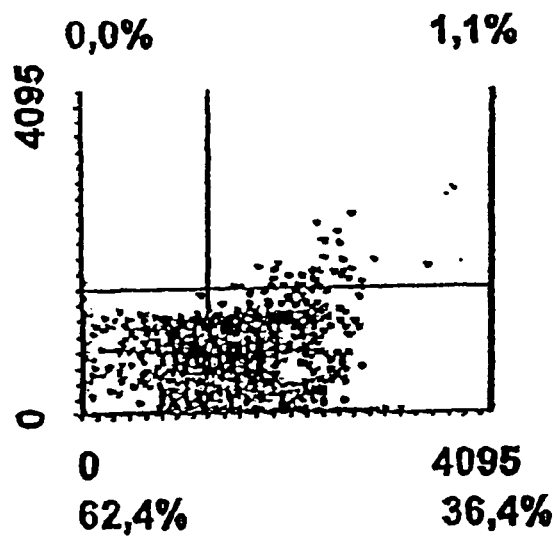
Figure 3F:
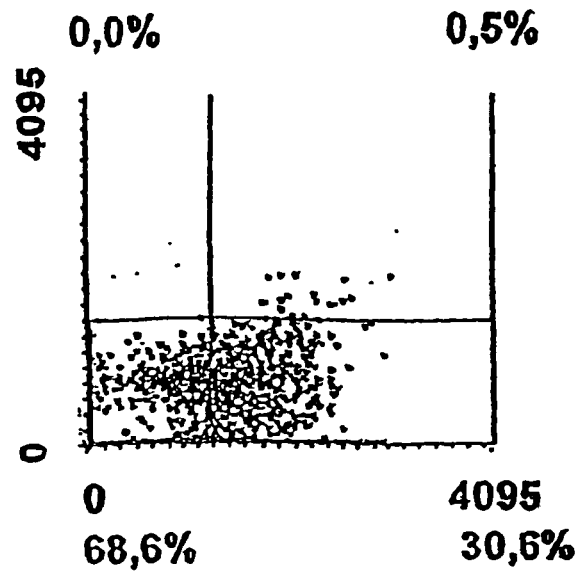

A further aspect of the present invention is a method for the synthesis of the novel 21-hydroxy-6,19-sulfanyl, and sulfoxy- and sulfonyl-progesterones of formula II (i.e. compounds 3-8).

Basically, the method for the preparation of the compound according to formula 3, comprises the steps of (see scheme 3):

a) providing the 19-thioacetylsteroid of formula 16 (see scheme 3)
b) protecting the 3-keto group thereof, preferably by a ethylene glycol group;
c) transforming the 19-thioacetyl group into a thiol group, and
d) performing a hydrolysis of the step c) compound.

The sulfoxy- and sulfonyl compounds 4 and/or 5, are generally obtained by
a) providing a compound of formula 3 (see scheme 4),
b) subjecting said compound to an oxidation, preferably with an oxidizing agent such as e.g ozone or potassium monopersulfate (for example Oxone®).

Treatment with potassium monopersulfate at low temperature (for example 0° C.) yields the sulfoxide, whereas treatment at room temperature yields the sulfone.

Preparation of the compound according to formula 6, comprises the steps of (see scheme 1)
a) providing the 19-hydroxyprogesterone of formula 11 (see formula in scheme 1);
b) transforming the 19-hydroxy group into a thioacetoxy group;
c) protecting the 3-keto group thereof, preferably by a ethylene glycol group;
d) transforming the 19-thioacetoxy group into a thiol group, and
e) performing a hydrolysis of the step d) compound The sulfoxy- and sulfonyl compounds 7 and/or 8, are generally obtained by
c) providing a compound according to formula 6,
d) subjecting said compound to an oxidation, preferably with an oxidizing agent such as potassium monopersulfate (for example Oxone®).

In the following a preferred method for the preparation of the 21-deoxy analogs 6, 7 and 8 shall be illustrated.

The following is a list of abbreviations used:
NBA: N-Bromoacetamide,
THF: Tetrahydrofuran,
VFC: Vapor flow Chromatography
PTSA: Para Toluene Sulfonic Acid
RT: Room Temperature.

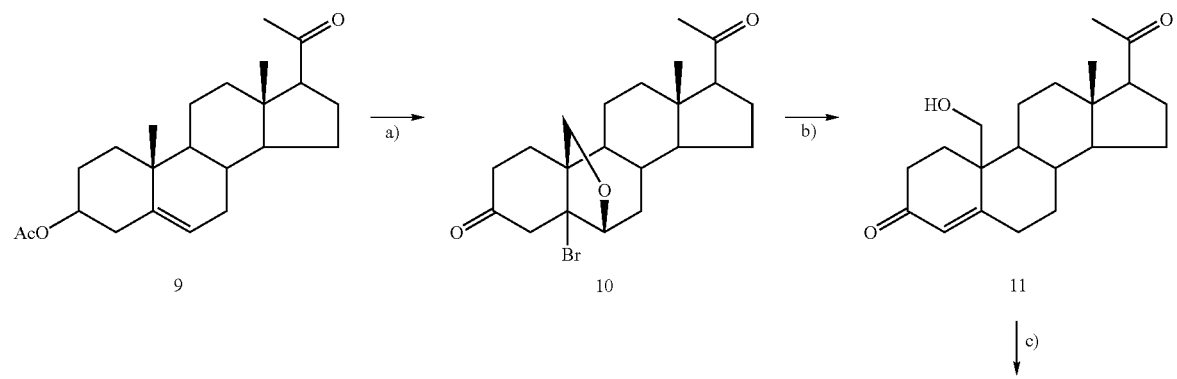

Scheme 1

-continued

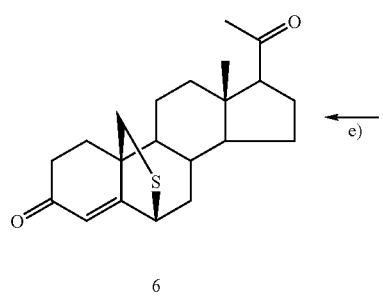

Steps
a) 1. NBA-HClO₄/THF-Et₂O 30 min, RT; 2. Diacetoxiiodobenzene, I₂, CH₂Cl₂, 300 W tungsten lamp, 2 h, RT;
3. NaOH, MeOH, 30 min, RT; 4. PCC, 4 Å molecular sieves, BaCO₃, CH₂Cl₂, RT.
b) Zn, AcOH, i-PrOH, 3 h, 70° (then VFC);
c) 1. Trifluoromethanesulfonic anhydride, pyridine, 1 h RT; 2. KSAc, acetone (anhydrous), N₂, overnight, RT (then VFC).
d) 1. Ethylene glycol, ethyl orthoformate, PTSA, 2 h, 60°, N₂; 2. K₂CO₃, MeOH, 1 h, RT, N₂.
e) I₂, Et₃N, CH₂Cl₂, 2 h, RT (then VFC).

Starting from pregnenolone acetate (9), the bromoether (10) is obtained, which is reductively cleaved with Zn/AcOH in isopropanol to give 19-hydroxyprogesterone (11). The 19-hydroxy group thereof is converted into the triflate and displaced with potassium thioacetate to give (12). To form the 6,19-bridge, the 4,5-double bond is dis-placed to the 5,6-position by formation of the 3-ethylene ketal. The thioacetate is hydrolyzed with a suitable base to give the free 19-thiol (13) which is immediately treated with iodine and triethylamine in dichloromethane. This gives rise to a cascade reaction (see scheme 2) which proceeds to the final product 6,19-sulfanyl-progesterone (6) without isolation of intermediates.

Formation of the oxidized derivatives 7 and 8 is accomplished by oxidation, preferably with potassium monopersulfate, such as Oxone® (provided by DuPont de Nemours) in aqueous methanol. Short reaction times and low temperature (0° C.) gives sulfoxide (7) (single stereoisomer), while longer reaction times at room temperature gives the sulfone 8.

An X ray structure analysis (see FIG. 1) shows the superposition of the X ray crystal structures of both compound (6) and the oxygen-bridged analog (21-deoxy-compound of formula I).

Scheme 2 shows the "one pot" iodocyclization/deprotection/dehydrohalogenation reaction of the 3-protected 19-sulfanyl-steroid as well as possible side reactions. The desired compound 18 can be isolated by chromatography or recrystallization.

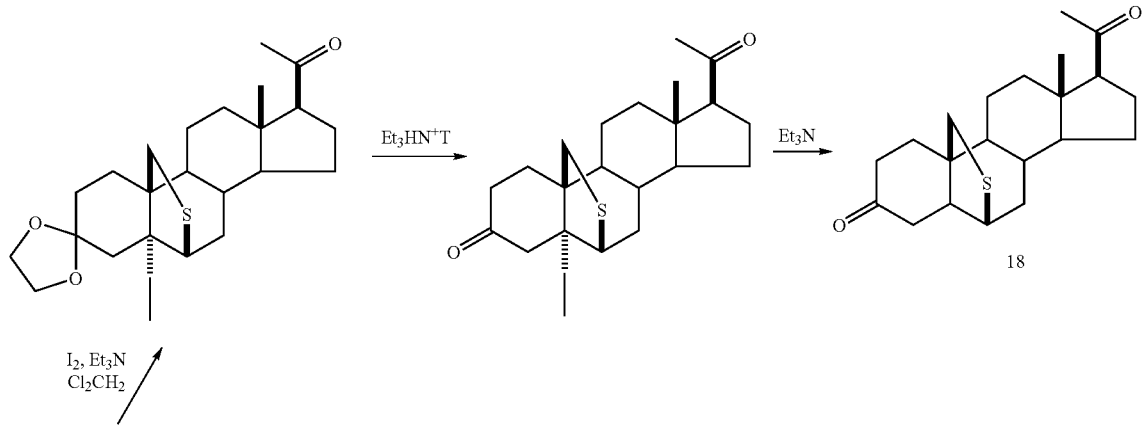

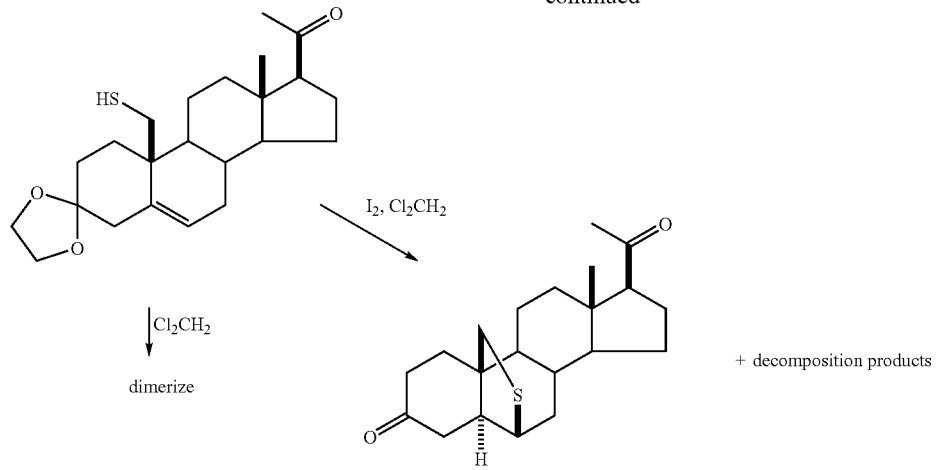

-continued

In the following a preferred method for the preparation of the 21-hydroxy analogs 3, 4 and 5 shall be illustrated.

The corresponding sulfur analogue of (1), i.e. 21-hydroxy-6,19-sulfanylprogesterone ((3); 21OH-6SP) is synthesized 19-hydroxy-deoxycorticosterone under the same reaction conditions. For the sake of simplicity the preferred synthetic procedure developed is shown starting from bromoketone (14).

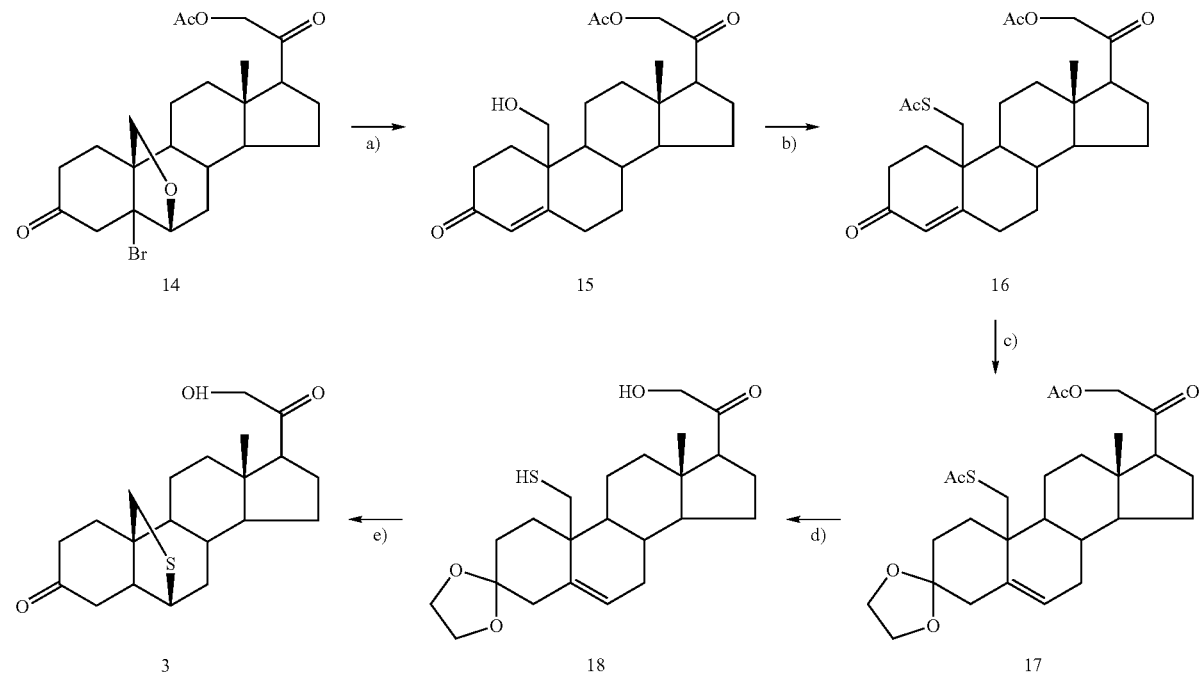

Steps
a) Zn-AcOH/iPrOH, 70° C. (VFC);
b) 1. (F$_3$CSO$_2$)$_2$O/py; 2. KSAc/Acetone;
c) Ethylene glycol (EtO)3CH/PTSA, (then VFC).
d) KOH/MeOH.
e) I$_2$, Et$_3$N, CH$_2$Cl$_2$, (then VFC).

together with the oxidized derivatives (4) and (5). The synthetic procedure starts from bromoketone (14) (see Scheme 3). Compound (14) may contain small amounts of the elimination product, however this does not affect yields, as both compound (14) and its elimination product are converted into The hydrolysis of the thioacetate in Scheme 3 is carried out simultaneously with the deacetylation at C-21 with KOH in methanol instead of potassium carbonate, as the latter reagent cleaves the α-ketolic side-chain being incompatible with 21-hydroxy-20-keto-steroids. Direct oxidation of (3) with potassium monopersulfate e.g: Oxone® affords the sulfoxide compound (4) and the sulfone compound (5) depending on the reaction conditions without affecting the side chain (Scheme 4).

The homogeneity of all compounds is confirmed by thin layer chromatography.

In the following examples 1 to 4, compound 14a is the starting compound, and compounds 14b, 14c and 14d are the intermediate compounds leading to the synthesis of compound 14 (5α-Bromo-21-acetyloxy-6,19-oxidopregnane-3,20-dione).

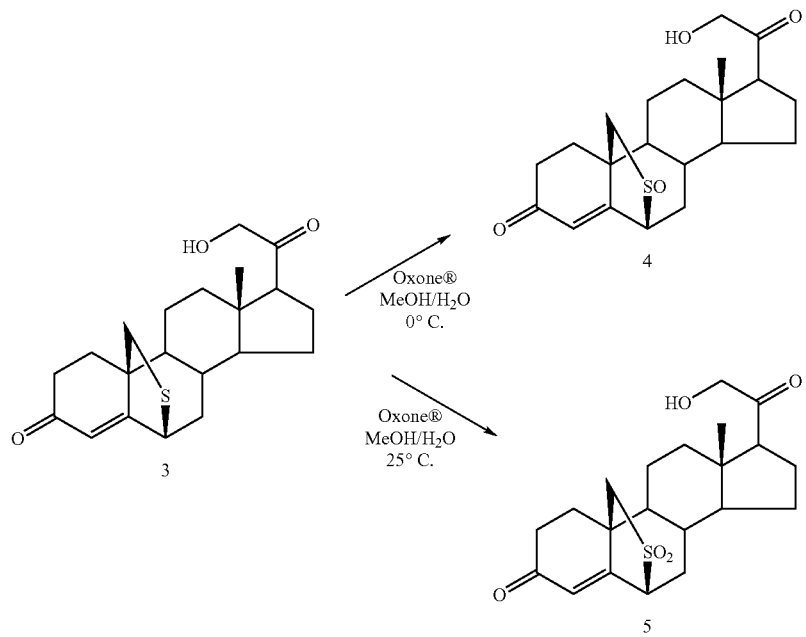

Scheme 4

The invention will now be further illustrated with the following examples:

EXAMPLES

Materials and Methods

Reagents:

General. Melting points. were taken on a Fisher-Johns apparatus and are uncorrected. IR spectra are recorded in thin films using KBr disks on a Nicolet Magna IR 550 FT-IR spectrometer. $^1$H and $^{13}$C NMR spectra are measured in Bruker AC-200 or AM-500 NMR spectrometers in deuteriochloroform (using TMS as internal standard). The J values are given in Hz. Spectra were assigned by analysis of the DEPT, COSY 45 and HETCOSY spectra and by comparison with those of progesterone.

The electron impact mass spectra (EI) are measured in a VG Trio 2 mass spectrometer at 70 eV by direct inlet FAB mass spectra and electron impact high resolution mass spectra (HRMS) are obtained in a VG ZAB BEQQ mass spectrometer. All solvents used are reagent grade. Solvents are evaporated at about 45° C. under vacuum. Zinc dust is activated by suspending it in 1M HCl, washing it with water, absolute ethanol and diethyl ether and drying 2 h at 120° C.

Example 1

3β-Formyloxy-21-acetyloxy-5-pregnen-20-one (14a)

Acetic anhydride (13.4 ml) is added dropwise to formic acid (6.6 ml) at 0° C., the solution is heated at 50° C. for 15 min and cooled rapidly to 0° C. The resulting acetoformic anhydride solution is added dropwise to a stirred suspension of 21-acetoxypregnenolone (commercially available, 8.0 g) in dry pyridine (20.8 ml) at 0° C., and stirring is continued at that temperature for 2 h. The reaction is poured over cold saturated aqueous sodium bicarbonate solution, filtered and the solid is washed with saturated aqueous sodium bicarbonate solution, water and 1N HCl and water (until neutral) to afford the formate title compound (8.0 g); $^1$H NMR (200.13 MHz) $\delta_H$ 0.70 (3H, s, 13-CH$_3$), 1.02 (3H, s, 10-CH$_3$), 2.16 (3H, s, 21-CH$_3$CO), 2.53 (1H, t, J=8.0 Hz, 17-H), 4.50 (1H, d, J=17.0 Hz, 21a-H), 4.70 (1H, d, J=17.0 Hz, 21b-H), 5.32 (1H, m, 3-H), 5.38 (1H, d, J=3.0 Hz, 6-H), 8.02 (1H, s, HCOO).

Example 2

3β-Formyloxy-5α-bromo-6β-hydroxy-21-acetyloxypregnan-20-one (14b)

Formate 14a (8.0 g), is dissolved in diethyl ether (100 ml) and THF (37.2 ml) and cooled to 10° C. To the stirred solution at 10-15° C. which protected from light −7.5% perchloric acid (11.88 ml) is added, followed by N-bromoacetamide (4.75 g) in 8 portions over a 25 min period. Stirring is continued for 45 min at 25° C. and the reaction is stopped by addition of 10% aqueous sodium thiosulfate solution until complete decoloration. The reaction mixture is then extracted with dichloromethane/methanol 10:1 and the organic layer, is washed with water, dried with anhydrous sodium sulfate and the solvent is evaporated to afford bromo-hydrin 14a (10.4 g, containing about 20% of the 5α-hydroxy-6β-bromo isomer as determined by $^1$H NMR).

Example 3

3β-Formyloxy-5α-bromo-21-acetyloxy-6,19-oxidopregnan-20-one (14c)

Nitrogen is bubbled for 5 min through a solution of bromohydrin compound 14b (10.4 g, containing about 20% of the 5α-hydroxy-6β-bromo isomer) in freshly distilled dichloro-methane (723 ml) contained in a 1 liter glass vessel fitted with an external cooling jacket with circulating water at 25° C. and magnetic stirrer. Diacetoxyiodobenzene (Suarez reagent, 7.66 g) and iodine (5.46 g) are successively added with stirring. The vessel is exposed to two 300 Watt tungsten lamps (5000 lm each) and vigorous stirring is continued for 1 h at 25° C. Irradiation is turned off and a saturated aqueous solution of sodium thiosulfate is added until complete decoloration. The organic layer is separated, dried with anhydrous sodium sulfate and the solvent evaporated. The resulting solid is dissolved in dichloro-methane (8 ml) and applied to a silicagel G-60 column (12 cm diameter×8 cm height) previously flushed with hexane; successive elution (applying vacuum to the outlet) with hexane-ethyl acetate 9:1 (1100 ml), 8:2 (700 ml), 7:3 (700 ml) and 6:4 (600 ml) affords 31×100 ml fractions. Fractions are analyzed by TLC and those containing bromoether 14c are pooled and evaporated to dryness to afford 14c (6.8 g). $^1$H NMR (200.13 MHz) $\delta_H$ 0.70 (3H, s, 13-CH$_3$), 2.16 (3H, s, 21-H$_3$CO), 2.52 (1H, t, J=8.8 Hz, 17-H), 3.73 (1H, d, J=8.4 Hz, 19a-H), 3.94 (1H, d, J=8.4 Hz, 19b-H), 4.08 (1H, d, J=4.2 Hz, 6-H), 4.50 (1H, d, J=16.8 Hz, 21a-H), 4.71 (1H, d, J=16.8 Hz, 21b-H), 5.34 (1H, m, 3-H), 8.02 (1H, s, HCOO).

Example 4

3β-Hydroxy-5α-bromo-21-acetyloxy-6,19-oxidopregnan-20-one (14d)

A stirred solution of the bromoether 14c (6.8 g) obtained above, is dissolved in dichloro-methane (45.7 ml) and methanol (154.7 ml) and is cooled to 0° C. in an ice bath and water (10.9 ml) while conc. HCl (23.0 ml) is added. After about 30 min of vigorous stirring at 0° C. (disappearance of the starting material is monitored by TLC) the reaction mixture is neutralized with 20% aqueous sodium hydroxide and extracted with dichloromethane. The organic layer is dried with anhydrous sodium sulfate and the solvent evaporated to afford the alcohol compound 14d (6.5 g); $^1$H NMR (200.13 MHz) $\delta_H$ 0.69 (3H, s, 13-CH$_3$), 2.16 (3H, s, 21-CH$_3$CO), 2.52 (1H, t, J=8.5 Hz, 17-H), 3.62 (1H, d, J=8.5 Hz, 19a-H), 3.92 (1H, d, J=8.5 Hz, 19b-H), 4.07 (1H, d, J=4.0 Hz, 6-H), 4.15 (1H, m, 3-H), 4.51 (1H, d, J=17.0 Hz, 21a-H), 4.70 (1H, d, J=17.0 Hz, 21b-H).

Example 5

5α-Bromo-21-acetyloxy-6,19-oxidopregnane-3,20-dione (14)

A suspension of pyridinium chlorochromate (12.1 g), barium carbonate (5.0 g) and 3 Å molecular sieves (9.60 g), in dry dichloromethane (480 ml) is stirred under nitrogen for about 10 min. To the resultant orange slurry a solution of bromoether 14d (6.5 g) obtained above in dry dichloromethane (324 ml) is added and stirring is continued for about 90 min until disappearance of starting material (TLC). The reaction mixture is percolated through a short silicagel G 60 column (12 cm diameter×8 cm height) washed with diethyl ether (2×150 ml) and hexane-ethyl acetate 1:2 (3×150 ml). Fractions containing the product are pooled and evaporated to dryness affording 5.5 g of ketone 14 (containing about 10% of $\Delta^4$-3-ketone); $^1$H NMR (200.13 MHz) $\delta_H$ 0.70 (3H, s, 13-CH$_3$), 2.16 (3H, s, 21-CH$_3$CO), 2.51 (1H, t, J=8.5 Hz, 17-H), 2.85 (1H, d, J=16.0 Hz, 4a-H), 3.40 (1H, d, J=16.0 Hz, 4b-H), 3.90 (1H, d, J=9.0 Hz, 19a-H), 4.07 (1H, d, J=4.0 Hz, 6-H), 4.15 (1H, d, J=9.0 Hz, 19b-H), 4.50 (1H, d, J=17.0 Hz, 21a-H), 4.71 (1H, d, J=17.0 Hz, 21b-H).

Following the synthetic procedures of examples 1-5, by using pregnenolone acetate instead of 21-acetyloxypregnenolone as starting compound in example 1, the corresponding 21-deoxy derivatives of 14 and 14a-d are obtained.

Example 6

19-Hydroxy-21-acetyloxy-4-pregnene-3,20-dione (15)

5α-Bromo-21-acetyloxy-6,19-oxidopregnane-3,20-dione (14) of Example 5 (2.5 gr, 5.4 mmol) is suspended in propan-2-ol (257 nm) at 70° C. Acetic acid (19.3 ml) and activated zinc dust (6.4 g, mmol) is added. The suspension is stirred and heated at 70-75° C. for 4 h, cooled, filtered, concentrated and extracted with dichloromethane. Chromatography on silicagel using hexane-ethyl acetate as eluant affords 19-hydroxy-21-acetoxyprogesterone (15) (1.1 g, 53%); $^1$H NMR (200.13 MHz) $\delta_H$ 0.70 (3H, s, 13-CH$_3$), 2.16 (3H, s, 21-CH$_3$CO) 2.50 (1H, t, J=8.0 Hz, 17-H), 3.89 (1H, d, J=10.8 Hz, 19a-H), 4.05 (1H, d, J=10.8 Hz, 19b-H), 4.50 (1H, d, J=16.8 Hz, 21a-H), 4.70 (1H, d, J=16.8 Hz, 21b-H), 5.95 (1H, s, 4-H).

Example 7

3,3-Ethylenedioxy-19-acetylsulfanyl-21-acetyloxy-5-pregnen-20-one (17)

A solution of 19-hydroxy-21-acetoxyprogesterone (15) (620 mg, 1.60 mmol) in cold pyridine (6.4 ml) is added dropwise to a stirred solution of trifluoromethanesulfonic anhydride (0.7 ml, 4.16 mmol) in cold pyridine (3.6 ml) under nitrogen. The solution is allowed to warm-up to room temperature and after 1 h cold dichloromethane (98.0 ml) is added. The reaction mixture is washed with cold 1M sulfuric acid, 5% aqueous sodium bicarbonate solution and water, dried and evaporated to dryness, yielding crude 19-triflylprogesterone-21-acetate, which is then mixed (780 mg, 1.60 mmol) and potassium thioacetate (780 mg, 6.83 mmol) in acetone (40.0 ml), and stirred at room temperature for 20 h under nitrogen. The reaction mixture is diluted with dichlorometane, filtered and evaporated to dryness affording crude 19-acetylsulfanylsteroid 16 (712 mg, 100%); $^1$H NMR (200.13 MHz) $\delta_H$ 0.74 (3H, s, 13-CH$_3$), 2.16 (31H, s, 21-CH$_3$CO), 2.32 (3H, s, 19-CH$_3$COS), 2.50 (1H, t, J=8.0 Hz, 17-H), 3.18 (1H, d, J=13.7 Hz, 19a-H), 3.47 (1H, d, J=13.7 Hz, 19b-H), 4.50 (1H, d, J=16.8 Hz, 21a-H), 4.70 (1H, d, J=16.8 Hz, 21b-H), 5.87 (1H, s, 4-H).

To a solution of compound 16 (460 mg, 1.03 mmol) in ethyleneglycol (0.55 ml, 9.9 mmol), ethyl ortoformate (0.80 ml, 4.8 mmol) and p-toluenesulfonic acid monohydrate (39.0 mg, 0.205 mmol) is added. The mixture was stirred for 2 h at room temperature under nitrogen, poured over saturated aqueous $NaHCO_3$ and extracted with dichloromethane. Column chromatography on silica gel with ethyl acetate-hexane as eluant yielded compound 17 (220 mg, 46%); $^1$H NMR 8H 0.70 (3H, s, 13-$CH_3$), 2.31 (3H, s, 19-$CH_3COS$), 2.50 (1H, t, J=8.4 Hz, 17-H), 3.03 (1H, d, J=14.0 Hz, 19a-H), 3.36 (1H, d, J=14.0 Hz, 1H), 3.94 (4H, m, ketal), 4.50 (1H, d, J=16.7 Hz, 21a-H), 4.70. (1H, d, J=16.7 Hz, 21b-H), 5.53 (1H, br d, J=2.7 Hz, 6-H).

Example 8

21-Hydroxy-6,19-sulfanyl-4-pregnene-3,20-dione (3)

Thioacetate 17 (88.0 mg, 0.19 mmol) is dissolved in dry methanol (2.5 ml) and the mixture deoxygenated by bubbling dry nitrogen 15 minutes. A solution of KOH (20 mg, 0.38 mmol) in methanol (0.14 ml) is added and the mixture is stirred at room temperature for 15 minutes. The reaction mixture is neutralized with 1N HCl, diluted with water, concentrated and extracted with dichloromethane. Evaporation of the solvent afforded the 19-sulfanyl derivative 18 (55.0 mg, 77%). To a solution of triethyl amine (0.022 ml, 0.16 mmol) and iodine (78.6 mg, 0.31 mmol) in dry dichloromethane (40 ml) cooled to 0° C., a solution of the thiol 18 (55 mg, 0.15 mmol) is added and the mixture stirred at 0° C. for 30 minutes and 2 hs at room temperature. Saturated aqueous sodium thiosulfate is added until a colorless mixture is obtained, and the reaction mixture is extracted with dichloromethane. Evaporation of the solvent followed by column chromatography on silica gel with ethyl acetate as eluant yields 21-hydroxy-6,19-sulfanyl 4-pregnene-3,20-dione (3,23 mg, 44%) $v_{max}$ (KBr)/$cm^{-1}$ 3465, 2938, 1712, 1676, 1070, 735; $^1$H NMR (500.13 MHz) $\delta_H$ 0.76 (3H, s, 13-$CH_3$), 2.46 (1H, t, J=93 Hz, 17-H), 2.57 (1H, d, J=10.7, 19a-H), 3.04 (1H, d, J=10.7, 19b-H), 3.90 (1H, dd, J=1.0 and 1.5 Hz, H-6), 4.16 (1H, d, J=11.0 Hz, 21a-H), 4.22 (1H, d, J=11.0 Hz, 21b-H), 5.79 (1H, s, H-4); $^{13}$C NMR see Table 9; EIMS m/z 360 (32) [M]$^+$, 344 (16), 329 (54), 301 (100), 153 (34), 91 (43), 43 (99).

Example 9

21-Hydroxy-6,19-sulfoxy-4-pregnene-3,20-dione (4)

To a solution of crude compound 3 (47.5 mg, 0.13 mmol) in methanol (4.3 ml) at 0° C. a solution of Oxone®, (127.4 mg, 0.40 mmol) in water (2.8 ml) is added. After stirring of 30 minutes at room temperature, the mixture is diluted with saturated aqueous sodium bisulfite, concentrated and extracted with dichlorometane. Purification by prep. TLC ($CH_2Cl_2$-MeOH 20:1) affords the sulfoxide 4 (24.0 mg, 48%); $v_{max}$(KBr)/$cm^{-1}$ 3458, 2938, 1719, 1667, 1077, 1041; $^1$H NMR (500.13 MHz) $\delta_H$ 0.68 (3H, s, 13-$CH_3$), 2.50 (1H, t, J=8.0 Hz, 17-H), 3.72 (1H, d, J=20.0 Hz, 19a-H), 3.88 (1H, d, J=20.0 Hz, 19b-H), 3.83 (1H, bt, 6-H), 4.18 (2H, bs, 21-H), 6.08 (1H, s, 4-H); $^{13}$C NMR see Table 9; EIMS m/z 376 (12) [M]$^+$, 359 (38), 345 (6), 313 (62), 159 (38), 91 (55), 55 (100), 41 (99).

Example 10

21-Hydroxy-6,19-sulfone-4-pregnene-3,20-dione (5)

To a solution of crude compound 3 (47.5 mg, 0.13 mmol) in methanol (4.3 ml) at 0° C. a solution of Oxone® (190.4 mg, 0.60 mmol) in water (4.3 ml) is added. After stirring for 24 hours at room temperature the mixture is diluted with saturated aqueous sodium bisulfite, concentrated and extracted with dichloromethane. Purification by prep. TLC ($CH_2Cl_2$-MeOH 20:1) affords the sulfone 5 (26.0 mg, 50%); $v_{max}$ (KBr)/$cm^{-1}$ 3465, 2945, 1712, 1676, 1305, 7420; $^1$H NMR (500.13 MHz) $\delta_H$ 0.75 (3H, s, 13-$CH_3$), 2.50 (1H, t, J=8.0 Hz, 17-H), 3.45 (1H, d, J=13.5 Hz, 19a-H), 3.98 (1H, d, J=13.5 Hz, 19b-H), 3.82 (1H, br s, 6-H), 4.19 (2H, bs, 21-H), 6.09 (1H, s, 4-H); EIMS m/z 392 (1) [M]$^+$, 361 (29), 333 (11), 267 (23), 253 (15), 91 (43), 55 (77), 43 (100).

Example 11

19-Hydroxy-4-pregnene-3,20-dione (11)

The 21-deoxy-6,19-bromoether 10 (2.09 g, 4.9 mmol), which corresponds to the 21-acetoxy-6,19-bromoether 14 obtainable according to the examples 1-5, is suspended in propan-2-ol (175 ml) and acetic acid (15.6 ml) and activated zinc dust (5.2 g) is added. The suspension is stirred and heated at 70-75° C. for 4 h, cooled, filtered, concentrated and extracted with dichloromethane. Chromatography on silica-gel using hexane-ethyl acetate as eluant affords 19-hydroxyprogesterone (11) (0.92 g, 53%), m.p. 165-168° C. (from methanol); $^1$H NMR identical to an authentic standard.

Example 12

3,3-Ethylenediox-19-acetylsulfanyl-5-pregnen-20-one

A solution of 19-hydroxyprogesterone (11) (522 mg, 1.58 mmol) in cold pyridine (5.2 ml) is added dropwise to a stirred solution of trifluoromethanesulfonic anhydride (0.7 ml, 4.16 mmol) in cold pyridine (3.6 ml) under nitrogen. The solution is allowed to warm to room temperature and after 1 h cold dichloromethane (95.0 ml) is added. The reaction mixture is washed with cold 1M sulfuric acid, 5% aqueous sodium bicarbonate solution and water, dried and evaporated to dryness, yielding crude triflate as an orange solid (680 mg, 100%); $^1$H NMR (200.13 MHz) $\delta_H$ 0.68 (3H, s, 13-$CH_3$), 2.12 (3H, s, 20-$CH_3$), 2.50 (1H, t, J=8.0 Hz, H-17), 4.68 (2H, qAB, J=10.0 Hz, 19-H), 5.00 (1H, s, H-4). A mixture of crude 19-triflylprogesterone (680 mg, 1.58 mmol) and potassium thioacetate (680 mg, 6.0 mmol) in acetone (35.0 ml), is stirred at room temperature for 20 h under nitrogen. The reaction mixture is diluted with dichlorometane, filtered and evaporated to dryness affording crude 19-acetylsulfanylsteroid 12 (614 mg, 100%); $^1$H NMR (200.13 MHz) $\delta_H$ 0.70 (3H, s, 13-$CH_3$), 2.12 (3H, s, 20-$CH_3$), 2.32 (3H, s, 19-$CH_3COS$), 2.55 (1H, t, J=8.7 Hz, H-17), 3.19 (1H, d, J=13.6 Hz, 19a-H), 3.49 (1H, d, J=13.6 Hz, 19b-H), 5.88 (1H, s, 4H); To a solution of 19-acetylsulfanylsteroid compound 12 (614 mg, 1.58 mmol) in ethylene-glycol (0.85 ml, 15.4 mmol), ethyl orthoformate (1.26 ml, 7.2 mmol) and p-toluenesulfonic acid (52.0 mg, mmol) are added. The mixture is stirred for 2 h at room temperature under nitrogen, poured over saturated aqueous $NaHCO_3$ and extracted with dichloromethane. Column chromatography on silica gel with ethyl acetate-hexane as eluant yields 3,3-ethylenedioxy-19-acetylsulfanyl-5-pregnen-20-one (256 mg, 63%); m.p. 151-153° C. (from EtAcO-hexane). (Found: C, 69.1; H, 8.4%; $C_{25}H_{36}O_4S$ requires C, 69.41; H, 8.39%); $v_{max}$ (KBr)/$cm^{-1}$; $^1$H NMR (200.13 MHz) $\delta_H$ 0.65 (3H, s, 13-$CH_3$), 1.62 (1H, m, 7α-H), 2.11 (3H, s, 20-$CH_3$), 2.31 (3H, s, 19-$CH_3COS$), 2.10 (1H, m, 7α-H), 2.53 (1H, t, J=8.8 Hz, H-17), 3.03 (1H, d, J=14.4 Hz, 19a-H), 3.37 (1H, d, J=14.4 Hz, 19b-H), 3.94 (4H, m, ketal), 5.53 (1H, brd, J=5.0 Hz, 6-H).

Example 13

6,19-Sulfanyl-4-pregnen-20-one (6)

The 3,3-ethylenedioxy-19-acetylsulfanyl-5-pregnen-20-one of Example 12 (64 mg, 0.16 mmol) is dissolved in dry methanol (1.8 ml) and the mixture deoxygenated by bubbling dry nitrogen through it for 15 minutes. A solution of KOH (14.5 mg, 0.28 mmol) in methanol (0.10 ml) is added and the mixture is stirred at room temperature for 15 minutes. The reaction mixture is then neutralized with 1N HCl, diluted with water, concentrated and extracted with dichloromethane. Evaporation of the solvent affords the 19-sulfanyl derivative 13 (45 mg, 77%); $^1$H NMR (200.13 MHz) $\delta_H$ 0.70 (3H, s, 13-CH$_3$), 1.25 (1H, dd, J=4.7 and 8.5 Hz, 19-HS), 1.63 (1H, m, 7α-H), 2.12 (1H, m, 7β-H), 2.77 (1H, t, J=8.5 Hz, 17-H), 2.56 (1H, dd, J=11.1 and 8.5, 19a-H), 3.07 (1H, dd, J=11.1 and 4.7, 19b-H), 3.94 (4H, m, ketal), 5.66 (1H, br d, J=5.0 Hz, H-6);

To a solution of triethyl amine (0.018 ml, 0.13 mmol) and iodine (63 mg, 0.25 mmol) in dry dichloromethane (32 ml) cooled to 0° C., a solution of the thiol 13 (45 mg, 0.12 mmol) is added and the mixture stirred at 0° C. for 30 minutes and then 2 hs at room temperature. Saturated aqueous sodium thiosulfate is added until a colorless mixture is obtained and the reaction mixture extracted with dichloromethane. Evaporation of the solvent followed by column chromatography on silica gel with ethyl acetate as eluant yielded 6,19-sulfanyl-4-pregnen-20-one (6) (19 mg, 46%); m.p. 183-185° C. (from EtAcO-hexane); (Found: C, 73.2; H, 8.4; S, 9.4%; C$_{21}$H$_{28}$O$_2$S requires C, 73.21; H, 8.19; S, 9.31); $\mu_{max}$ (KBr)/cm$^{-1}$ 2945, 1712, 1667, 1362, 1191, 742; $^1$H NMR (200.13 MHz) $\delta_H$ 0.74 (3H, s, 13-CH$_3$), 1.62 (1H, m, 7α-H), 1.99 (1H, m, 7β-H), 2.12 (3H, s, 20-CH$_3$), 2.50 (1H, t, J=8.0 Hz, 17-H), 2.57 (1H, d, J=10.5 Hz, 19a-H), 3.05 (1H, d, J=10.5 Hz, 19b-H), 3.89 (1H, dd, J=2.2 and 3.6, 6-H), 5.80 (1H, s, 4-H); EIMS m/z 344 (3) [M]$^+$, 254 (5), 149 (5), 84 (50), 49 (100)

Example 14

6,19-Sulfoxy-4-pregnene-3,20-dione (7)

To a solution of crude compound 6 (20.0 mg, 0.06 mmol) in methanol (1.9 ml) at 0° C. a solution of Oxone® (56.9 mg, 0.18 mmol) in water (1.26 ml) is added After stirring 30 minutes at room temperature the mixture is diluted with saturated aqueous sodium bisulfite, concentrated and extracted with dichloromethane. Purification by prep TLC (CH$_2$Cl$_2$-MeOH 20:1) afforded 6,19-sulfoxy-4-pregnen-3,20-dione (7, 9.5 mg, 45%); $\nu_{max}$ (KBr)/cm$^{-1}$ 2938, 1705, 1669, 1362, 1177, 1035, 735; $^1$H NMR (200.13 MHz) $\delta_H$ 0.70 (3H, s, 13-CH$_3$), 2.11 (3H, s, 20-CH$_3$), 2.50 (1H, t, J=8.0 Hz, 17-H), 3.75 (1H, d, J=24 Hz, 19a-H), 3.98 (1H, d, J=24 Hz, 19b-H), 3.83 (1H, bt, J=2.2 and 3.6, 6-H), 6.07 (1H, s, 4H); EIMS m/z 360 [M]$^+$ (1.3), 345 (1), 344 (3), 312 (1), 297 (6), 255 (5), 43 (100).

Example 15

6,19-Sulfone-4-pregnene-3,20-dione (8)

To a solution of crude compound 6 (20.0 mg, 0.06 mmol) in methanol (1.9 ml) at 0° C. a solution of Oxone® (87.9 mg, 0.27 mmol) in water (3.0 ml) is added. After stirring 24 hs at room temperature the mixture is diluted with saturated aqueous sodium bisulfite, concentrated and extracted with dichloromethane. Purification by prep. TLC (CH$_2$Cl$_2$-MeOH 20:1) afforded 6,19-sulfone-4-pregnene-3,20-dione (8, 10.0 mg, 44%); $\nu_{max}$ (KBr)/cm$^{-1}$ 2945, 1697, 1312, 1134, 735; $^1$H NMR (500.13 MHz) $\delta_H$ 0.73 (3H, s, 13-CH$_3$), 2.12 (3H, s, 20-CH$_3$), 2.50 (1H, t, J=8.0 Hz, 17-H), 2.98 (1H, d, J=13.3 Hz, 19a-H), 3.46 (1H, d, J=13.3 Hz, 19b-H), 3.83 (1H, t, J=2.6, 6-H), 6.09 (1H, s, 4-H); EIMS m/z 376 [M]$^+$ (4), 358 (1), 343 (1), 344 (1) 329 (1), 312 (13), 279 (1.5)

BIOLOGICAL ASSAYS

I. Anti-Immunosuppressing Activity:

Cell Assay: Apoptosis in Rat Thymocytes
a) Rationale:
Analysis of cell death (in vitro):
Glucocorticoids have been shown to induce thymocyte apoptosis (J. Exp. Med. 184(5) p. 1631-8, 1996 Nov. 1). On this basis, the antiglucocorticoid properties of the compounds of the present invention may be determined by examining the decrease/increase of apoptosis in rat thymocytes after treatment with a given test compounds.

Hence, the experiments were carried out in order to evaluate the apoptosis-blocking capacity of the sulfanyl analog (3), the sulfoxy analogs (4) and the sulfone analog (5) and compared with the activity of 21OH-6OP (I). The experiments show that the tested analogs were either equally effective at $10^{-4}$ M or more active than 21OH-6OP (I).

Regulation of apoptosis was analyzed by flow cytometry. The method consists of quantitying fluorometrically the apoptotic cells in the sample. In normal viable cells phosphatidyl serine (PS) is located on the cytoplasmic surface of the cell membrane. Upon induction of apoptosis, rapid alteration in the organization of phospholipids in most cell types occurs leading to exposure of PS on the cell surface. In vitro detection of externalized PS may be achieved through interaction with the anticoagulant annexin V. In the presence of calcium, rapid high affinity binding of annexin V to PS occurs. PS translocation to the cell surface precedes nuclear breakdown, DNA fragmentation and the appearance of most apoptosis-associated molecules making annexin V binding a marker of early-stage apoptosis.

In the assay used, a fluorescein isothiocyanate (FITC) conjugate of annexin V is used allowing detection of apoptosis by flow cytometry. Since membrane permeabilization is observed in necrosis, necrotic cells will also bind annexin V-FITC. Propidium iodide is used to distinguish between viable and early apoptotic cells thus the latter will be labeled only with FITC while late apoptotic cells will be labeled with FITC and propidium iodide.

b) Methodology:
An annexin V-FITC apoptosis detection kit from Oncogen Research Products (cat. No. PF032) was used following the RAPID protocol recommended by the manufacturer. Briefly, after incubation with various compounds (see below), cells were centrifuged at 2000 rpm for 5 min, the media removed and cell pellets washed with phosphate buffered saline (PBS): Cells were resuspended in the binding buffer to a density of $1 \times 10^6$ cells/ml. Binding reagent (10 µl) and annexin V/FITC (1.25 µl) were added and cells incubated for 15 min at room temperature in the dark. The cells were centrifuged and to the pellet were added binding buffer (0.5 ml) and propidium iodide (10 µl). Samples were analyzed by flow cytometry in a Cytoron Absolute cytometer (Ortho Diagnostic Systems). Data were analyzed with Wimdi 2.7.

c) Results:
The above protocol was used to analyze cell apoptosis induced in thymocytes incubated with dexamethasone (which induces apoptosis) $10^{-8}$ M alone and in the presence of the test compounds. RU-486 (11-(4-Dimethylamino-phenyl)-17-hydroxy-13-methyl-17-prop-1-ynyl-1,2,6,7,8,11,12,13,14,15,16,17-dodecahydro-cyclopenta[α]phenanthren-3-one) at $10^{-6}$ M was used as positive control (reference compound); the test compounds were tested at $10^{-5}$ M. Thymocytes were incubated in the presence of dexamethasone and the corresponding test compounds (3), (5) and (8) for 4 b at 37° C. and then processed as indicated above.

The cytograms obtained are presented in FIGS. 3a-3f, where GR-FL represents fluorescence from FITC and RD-FL represents fluorescence from propidium iodide. Viable cells which do not bind annexin-FITC nor propidium iodide appear in the lower quadrant/left. Early apoptotic cells with exposed PS but intact cell membranes appear in the lower left quadrant. Necrotic or late apoptotic cells appear in the upper right quadrant. A small percentage of normal cell death may also occur, none is observed in this case.

In the following Table 1, the percentage of total apoptosis observed (early apoptosis+late apoptosis) is reported for each compound.

TABLE 1

| Steroids | % total apoptosis |
|---|---|
| Dexamethasone $10^{-8}$M | 40.40% |
| Dexamethasone $10^{-8}$M + RU-486 $10^{-6}$M | 35.50% |
| Dexamethasone $10^{-8}$M + 21OH-6OP (2) $10^{-5}$M | 38.10% |
| Dexamethasone $10^{-8}$M + 21OH-6SP (3) $10^{-5}$M | 37.50% |
| Dexamethasone $10^{-8}$M + 21OH-6SOP (4) $10^{-5}$M | 34.60% |
| Dexamethasone $10^{-8}$M + 21OH-6SO$_2$P (5) $10^{-5}$M | 31.40% |

II. Expression of a Reporter Gene: (Reporter Gene Assay):

pMMTV (Mouse Mammary Tumor Virus) Luc (Luciferase) Expression in Cos-1 Line

A general description of a reporter gene assay may be found in *Biotechniques vol.* 7 No. 10 (1989). The assay may discriminate between gluco/antigluco- and progestin/anti-progestin-effects of the test compounds. Cells were grown on 100 mm plates with 8 ml D-MEM (Dubecco's modified Eagle's medium Gibco BRL), supplemented with 10% bovine fetal serum (Bioser), 3.7 g/l sodium bicarbonate and 100 IU/penicilin G, 100 µg/ml streptomycin, 0.25 µg amphotericin B in an atmosphere in an of 5% $CO_2$ at 37° C. Cells were treated with 0.25% trypsin, 1 mM EDTA and were plated at a density of 5×10$^5$ cells/plate, in 60 mm plates. Cos-1 cells were transfected with a construct encoding the glucocorticoid receptor, and a construct with the luciferase gene under the MMTV promoter. Cells were transfected by precipitation with calcium phosphate adding 25 µl of a 2M CaCl$_2$ solution to a solution containing 3 pmoles of vectors pMMTV-Luc and pRSV-GR encoding luciferase and the glucocorticoid receptor, respectively. The mouse mammary tumor virus (MMTV) promoter is induced by glucocorticoid hormone via the glucocorticoid receptor (GR) (*EMBO* June 1 20(11), p. 2802-11 (2001)). PRSV-lacZ vector was used as control of transfection.

The transfection mixture was added dropwise to an equal volume of transfection buffer 2×BBS, containing phosphate. 500 µl of the total mixture were added to each plate and incubated during 16 h Cells were washed and treated with dexamethasone in a medium containing 10% steroid-free serum during 36 h. After incubation, cells were washed twice with TBS. 300 µl lysis buffer was added to each plate and incubated during 15 nm at room temperature. From the supernatant the luciferase activity was determined. Beta-galactosidase activity was used as an internal standard. Luciferase expression was assayed employing a Promega kit in partial obscurity and measured with a Junior luminometer (EG&G Berthold, Germany).

β Galactosidase was determined by hydrolysis of a phenyl galactoside.

As shown in FIG. 4, the use of test compounds (4) (i.e. 21OH-6,19 SP) at $10^{-6}$ M concentration provides for about 65% of reduction of the luciferase/β galactosidase ratio. RU486 was used as positive control. This experiment confirms the inhibiting action of the sulfoxide 21OH-SOP (4), at the glucocorticoid receptor. None of the tested steroids showed effect per se when used in the absence of dexamethasone, i.e. they are not agonists at the glucocorticoid receptor, under the experimental conditions.

The invention claimed is:

1. A method for reducing thymocyte apoptosis in a human in need thereof, comprising
administering a composition comprising a compound of formula (IIa) and one or more pharmaceutically acceptable carriers or diluents to the human in need thereof,

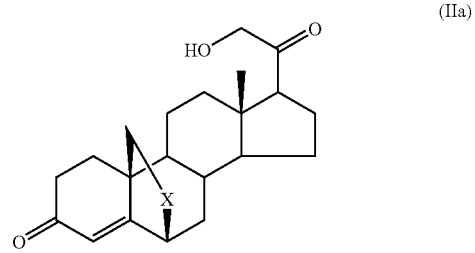

(IIa)

wherein X is S, SO or SO$_2$, in an amount effective for reducing thymocyte apoptosis.

2. A method for reducing thymocyte apoptosis in a human in need thereof, comprising
administering a composition comprising a compound of formula (II) and at least one pharmaceutically acceptable carrier or diluent to the human in need thereof,

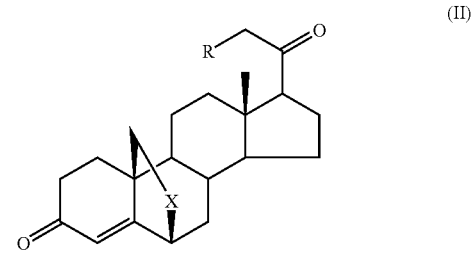

(II)

wherein X is S, SO, or SO$_2$, and R is H or OH, in an amount sufficient to reduce the apoptosis.

* * * * *